United States Patent [19]

Huffman

[11] Patent Number: 4,458,085

[45] Date of Patent: Jul. 3, 1984

[54] PREPARATION OF 3-BENZOTHIENYLGLYCINES

[75] Inventor: George W. Huffman, Carmel, Ind.

[73] Assignee: Eli Lilly and Company, Indianapolis, Ind.

[21] Appl. No.: 484,127

[22] Filed: Apr. 12, 1983

[51] Int. Cl.³ .................. C07D 333/60; C07D 333/64
[52] U.S. Cl. ......................... 549/51; 549/54; 549/55; 549/57; 549/58
[58] Field of Search .................. 549/51, 54, 55, 57, 549/58

[56] References Cited

U.S. PATENT DOCUMENTS 2,517,826  8/1950  Avakian et al. ...................... 549/58

OTHER PUBLICATIONS

Ben-Ishai et al., Chem. Comm., J.C.S. 1975 (pp. 349–350).
Ben-Ishai et al., Tetrahedron, 32, 1976 (1571–1573).
Ben-Ishai et al., Tetrahedron, 32, 1977 (2715–2717).
Ben-Ishai et al., Tetrahedron, 34, 1978 (467–473).
Sadeh et al., J. Heterocyclic Chem., 18, 1605 (1981).

*Primary Examiner*—Richard Raymond
*Attorney, Agent, or Firm*—Charles W. Ashbrook; Arthur R. Whale

[57] ABSTRACT

3-Benzothienylglycines are prepared by reaction of a benzothiophene with an α-hydroxyglycine derivative in the presence of trifluoroacetic acid.

10 Claims, No Drawings

PREPARATION OF 3-BENZOTHIENYLGLYCINES

BACKGROUND OF THE INVENTION

α-Amino-α-benzothienylacetic acids (benzothienylglycines) are known compounds, and have been employed in the synthesis of compounds that are useful as antibiotics; see U.S. Pat. No. 3,575,969. The synthesis of benzothienylglycines has been accomplished by several routes, including reduction of α-oximino-α-benzothienyl acetic acids that are derived from benzothienylglyoxylic acids; see British Pat. No. 1,399,089. Benzothienylglycines also have been prepared by treatment of a benzothienyl aldehyde with sodium cyanide and ammonium chloride, followed by hydrolysis. This is known as the Strecker synthesis.

All of these synthetic procedures suffer from being non-selective and low-yielding. An object of the present invention is to provide a process that produces 3-benzothienylglycine derivatives in high yield and high purity.

SUMMARY OF THE INVENTION

This invention concerns a chemical process for preparing 3-benzothienylglycines. The invention is more particularly directed to a process for preparing a compound of the formula

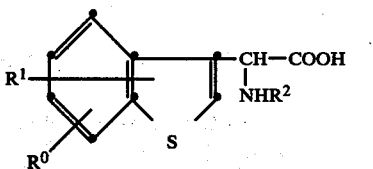

wherein:
$R^0$ and $R^1$ independently are hydrogen, $C_1$-$C_4$ alkyl, $C_1$-$C_4$ alkoxy, hydroxy, halo, nitro, $C_1$-$C_4$ alkanoylamino or $C_1$-$C_4$ alkylsulfonylamino;
$R^2$ is an amine protecting group; comprising reacting a benzothiophene of the formula

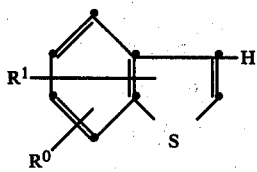

with an α-hydroxyglycine of the formula

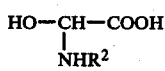

in the presence of trifluoroacetic acid.

In a preferred embodiment of the invention, $R^2$ is an amine protecting group such as chloroacetyl, or allyloxycarbonyl.

DETAILED DESCRIPTION OF THE INVENTION

The process of this invention employs a benzo[b]thiophene as a substrate. The benzothiophene can be unsubstituted, or it can be mono- or di-substituted at the 2, 4, 5, 6 or 7 position with groups such as $C_1$-$C_4$ alkyl, $C_1$-$C_4$ alkoxy, hydroxy, halo, nitro, amino, $C_1$-$C_4$ alkanoylamino or $C_1$-$C_4$ alkylsulfonylamino. The term "$C_1$-$C_4$ alkyl" carries its art-recognized meaning of straight and branched aliphatic groups such as methyl, ethyl, n-propyl, iso-propyl, n-butyl, and tert.-butyl. "$C_1$-$C_4$ Alkoxy" refers to lower alkyl groups linked through oxygen, for example methoxy, ethoxy, isopropoxy and sec-butoxy. "$C_1$-$C_4$-Alkanoylamino" means a lower alkanoyl group such as formyl, acetyl, or butyryl linked to a nitrogen atom which in turn is bonded to the benzothiophene. "$C_1$-$C_4$-alkylsulfonylamino" includes groups such as methylsulfonylamino and isobutylsulfonylamino. "Halo" as used herein includes fluoro, chloro, bromo and iodo.

Typical benzothiophenes that can be employed in the process of this invention include 2-chlorobenzothiophene, 2-methoxybenzothiophene, 4-bromobenzothiophene, 5-methylbenzothiophene, 6-nitrobenzothiophene, 7-acetylaminobenzothiophene, 2,4-dichlorobenzothiophene, 2-fluoro-5-ethoxybenzothiophene, 4,7-di-n-butylbenzothiophene, 5-chloro-6-nitrobenzothiophene and the like.

The process of this invention can be carried out by combining approximately equimolar quantities of a benzothiophene and an α-hydroxy glycine of the formula

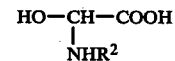

wherein $R^2$ is an amino protecting group. The term "amino protecting group" as used herein means any group that is substantially stable to trifluoroacetic acid and is readily removed when desired. Such groups will be employed during the process to minimize any undesired side reactions that might otherwise occur. Such amino protecting groups also aid in enhancing solubility of the hydroxyglycine. Amine protecting groups are more fully discussed by J. W. Barton in "Protective Groups in Organic Chemistry", J. F. McOmie, Ed., Plenum Press, New York, N.Y., 1973, Chapter 2. That discussion is incorporated herein by reference as exemplary of the term.

Typical amino protecting groups as defined by $R^2$ in the above formula include substituted carbonyl moieties such as allyloxycarbonyl, methoxycarbonyl, benzyloxycarbonyl, 4-nitrobenzyloxycarbonyl, 2,2,2-trichloroethoxycarbonyl, chloromethoxycarbonyl, benzoyl, 4-nitrobenzoyl, acetyl, formyl, trichloroacetyl; alkenyl groups such as allyl, 1-carbomethoxy-2-propenyl, and related groups.

While in carrying out the process of this invention, approximately equimolar quantities of the benzothiophene and the α-hydroxyglycine derivative are normally employed, such amounts are not critical, and an excess of either substrate can be used if desired. Any such excess may be from about 0.1 to about 1.0 molar excess, although larger excesses are not detrimental.

The process is carried out in trifluoroacetic acid as reaction solvent and catalyst. The trifluoroacetic acid preferably is employed in concentrated form, and normally is used in an amount sufficient to facilitate convenient handling of the reaction. The process typically is conducted at a temperature of about 0° to about 75° C., although reaction temperature is not critical. The reaction normally is substantially complete after about 2 to about 24 hours, although longer reaction periods are not detrimental to the process and can be employed if desired.

Isolation of the product, a 3-benzothienylglycine derivative, is readily accomplished if desired by simply removing the reaction solvent, for instance by evaporation under reduced pressure. The product can be purified if needed by standard methods such as acid and base extraction. For example, the product can be suspended in water and extracted into a water immiscible solvent such as ethyl acetate or chloroform. The product, being a carboxylic acid derivative, readily forms water soluble alkali metal salts such as the sodium or potassium salts. These salts can be crystallized or can be converted back to the free acid. The free acid can be crystallized from common solvents such as acetone, chloroform, dichloromethane and the like.

It will be noted that the compounds prepared by the process of this invention have at least one asymmetric carbon atom, and thus exist in more than one optical form. The process can be carried out employing a racemic mixture of α-hydroxyglycine derivative, thereby providing a racemic mixture of benzothienylglycine product. Alternatively, if an optically active benzothienylglycine is desired, separation of the racemic mixture can be accomplished by conventional methods, including chromatography, crystallization, enzymatic separation, and racemization, for instance by the method of U.S. Pat. No. 3,976,680.

The process of this invention permits the facile synthesis of otherwise difficult to prepare benzothienylglycines. The process is specific in that the reaction proceeds substantially exclusively at the benzothiophene 3-position. The reaction is also high yielding, and yields of about 75 to about 95 percent of desired benzothienylglycine are typical.

The 3-benzothienylglycines that are prepared according to the method of this invention are useful as chemical intermediates. For example, the compounds can be coupled to a cephalosporin nucleus such as 7-amino-3-methyl-3-cephem-4-carboxylic acid by standard techniques. Removal of any protecting groups then provides a 7-(3-benzothienylglycylamido)-3-methyl-3-cephem-4-carboxylic acid, a potent agent useful for treating diseases caused by gram positive and gram negative microorganisms.

The following detailed examples are presented by way of further illustration of the present invention.

EXAMPLE 1

N-Allyloxycarbonyl-(3-benzothienyl)glycine

A solution of 5.15 g. (29.4 mM) of DL N-allyloxycarbonyl-α-hydroxyglycine and 3.95 g. (29.4 mM) of benzo[b]thiophene in 40 ml. of trifluoroacetic acid was stirred at 22.5° C. for eighteen hours. The reaction mixture was then concentrated by evaporation under reduced pressure to give an oil, and the oil was dissolved in a mixture of 100 ml. of ethyl acetate and 100 ml. of water. The organic layer was separated, and the aqueous layer was extracted twice more with 50 ml. portions of fresh ethyl acetate. The organic extracts were combined, washed with water, and then extracted twice with 100 ml. portions of 10% aqueous sodium bicarbonate. The aqueous extracts were combined, added to 100 ml. of fresh ethyl acetate, and acidified to pH 2.0 by the addition of conc. hydrochloric acid. The organic layer was separated and the aqueous acid layer was extracted with two 50 ml. portions of fresh ethyl acetate. The organic portions were combined, dried, and the solvent was removed by evaporation to provide 7.55 g. (88% yield) of N-allyloxycarbonyl-(3-benzothienyl)glycine.

Analysis calc. for $C_{14}H_{13}NO_4S$:
Theory: C, 57.92; H, 4.50; N, 4.81; O, 21.97; S, 11.27.
Found: C, 57.98; H, 4.57; N, 4.54; O, 21.80; S, 11.27.
Mass Spec. M+ Theory 291; Found 291.
$pK_a$ (66% aqueous DMF) 5.70.
IR (KBr mull) 3313, 1711, 1683, 1543, 1420, 1312 $cm^{-1}$.

EXAMPLE 2

N-Allyloxycarbonyl-[3-(5-methoxy)benzothienyl]glycine

A solution of 164 mg. (1 mM) of 5-methoxybenzothiophene and 175 mg. (1 mM) of D,L-N-allyloxycarbonyl-α-hydroxyglycine in 5 ml. of trifluoroacetic acid was stirred at 24° C. for sixteen hours. The reaction mixture was diluted by addition of 20 ml. of ethyl acetate, and then was concentrated to a solid by removal of the solvent by evaporation. The solid was crystallized from dichloromethane and cyclohexane to give 57 mg. of N-allyloxycarbonyl-[3-(5-methoxy)benzothienyl]glycine.

NMR ($DMSOd_6$): δ4.52 (d, 2H); δ5.18 (d, 1H); δ5.30 (d, 1H); δ5.59 (d, 1H); δ5.9 (m; 1H); δ7.41 (m, 2H); δ7.75 (s, 1H); δ7.90 (d, 1H); δ8.00 (d, 1H); δ8.20 (d, 1H); δ13.00 (s, 1H).

EXAMPLE 3

N-Ethoxycarbonyl-[3-(5-methoxy)benzothienyl]-glycine

A solution of 1.0 g. (6.13 mM) of N-ethoxycarbonyl-α-hydroxyglycine and 1.0 g. (6.09 mM) of 5-methoxybenzothiophene in 35 ml. of trifluoroacetic acid was stirred at room temperature for forty-eight hours. The solution was diluted by addition of 50 ml. of ethyl acetate, and the mixture was then extracted with 1N sodium hydroxide. The alkaline extracts were combined, washed with fresh ethyl acetate, acidified to pH 2 with 1N hydrochloric acid, and then extracted with fresh ethyl acetate. The organic extracts were combined, washed with water, dried, and the solvent was removed by evaporation under reduced pressure to give N-ethoxycarbonyl-[3-(5-methoxy)benzothienyl]glycine.

EXAMPLE 4

N-Chloroacetyl-[3-(5-methoxy)benzothienyl]-glycine

Following the procedure of Example 3, 3.0 g. (18.3 mM) of 5-methoxybenzothiophene were reacted with 3.0 g. (17.96 mM) of N-chloroacetyl-α-hydroxyglycine in 50 ml. of trifluoroacetic acid to provide, following crystallization from ethyl alcohol, N-chloroacetyl-[3-(5-methoxy)benzothienyl]glycine.

NMR ($DMSOd_6$): δ4.20 (s, 2H); δ5.78 (d 1H); δ7.46 (m, 2H); δ7.78 (s, 1H); δ7.90 (d, 1H); δ8.04 (d, 1H); δ9.10 (d, 1H); δ13.20 (s, 1H).

EXAMPLE 5

D,L-7-(3-Benzothienylglycylamido)-3-methyl-3-cephem-4-carboxylic acid

A solution of 5.82 g. (20 mM) of D,L-N-allyloxycarbonyl-(3-benzothienyl)glycine (for in Example 1) in 200 ml. of tetrahydrofuran containing 5.18 g. (21 mM) of N-ethoxycarbonyl-2-ethoxy-1,2-dihydroquinoline was added in one portion to a solution of 5.6 g. (24 mM) of allyl 7-amino-3-methyl-3-cephem-4-carboxylate in 200 ml. of acetonitrile. The reaction mixture was stirred at 25° C. for sixteen hours, and then concentrated to an oil by evaporation of the solvent. The oil was dissolved in 1 liter of ethyl acetate, washed once with 500 ml. of water, twice with 250 ml. portions of 5% aqueous sodium bicarbonate, twice with 5% hydrochloric acid, again with 250 ml. of water, and finally with 250 ml. of brine. The solution was dried and the solvent was removed by evaporation under reduced pressure to give 10.47 g. (99% yield) of D,L-allyl 7-N-allyloxycarbonyl-(3-benzothienyl)glycylamido-3-methyl-3-cephem-4-carboxylate.

Analysis calc. for $C_{25}H_{25}N_3O_6S_2$.
Theory: C, 56.91; H, 4.70; N, 7.96.
Found: C, 57.09; H, 4.94; N, 7.79.

NMR (DMSOd$_6$): δ2.00 and 2.05 (two singlets, 3H, D and L isomers); δ3.48 (m, 2H); δ7.8-8.05 (m, 5H); δ9.2 (m, 1H).

A solution of 72 mg. (0.32 mM) of lead tetraacetate in 50 ml. of acetone containing 419 mg. (1.6 mM) of triphenylphosphine was stirred at 25° C. for thirty minutes, and then was cooled to 5° C. and diluted by addition of 30 ml. of acetone containing 6.74 g. (12.8 mM) of DL-allyl 7-N-allyloxycarbonyl-(3-benzothienyl)-glycylamido-3-methyl-3-cephem-4-carboxylate (from above). The cold reaction mixture was stirred for ten minutes, and then 7.36 ml. (28.2 mM) of tributyl tin hydride were added in one portion. The reaction mixture was stirred for one hour at 0°-5° C. and then was diluted by addition of 5 ml. of 1N hydrochloric acid and stirred for an additional ten minutes. The reaction mixture was added to 25 ml. of water and washed twice with 50 ml. portions of n-hexane, and then the pH was adjusted to 4.5 with 1N sodium hydroxide. Concentration of the solution by evaporation of the organic solvent effected precipitation of a product that was collected by filtration and lyophilized to provide 4.12 g. (80% yield) of DL-7-(3-benzothienyl)glycylamido-3-methyl-3-cephem-4-carboxylic acid. A sample of the product thus formed (3.615 g.) was purified further by high pressure liquid chromatography to give 522.5 mg. of the L-isomer and 1.075 g. of D-7-(3-benzothienyl)-glycylamido-3-methyl-3-cephem-4-carboxylic acid.

Analysis calc. for $C_{18}H_{17}N_3O_4S_2$.
Theory: C, 53.58; H, 4.25; N, 10.41.
Found: C, 53.94; H, 4.22; N, 10.62.

I claim:
1. A process for preparing a compound of the formula

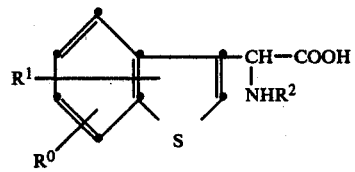

wherein:
$R^0$ and $R^1$ independently are hydrogen, $C_1$-$C_4$ alkyl, $C_1$-$C_4$ alkoxy, hydroxy, halo, nitro, $C_1$-$C_4$ alkanoylamino or $C_1$-$C_4$ alkylsulfonylamino;
$R^2$ is an amine protecting group; comprising reacting a benzothiophene of the formula

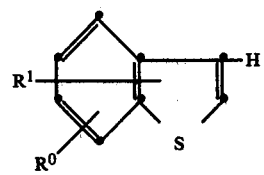

with an α-hydroxyglycine of the formula

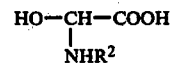

in the presence of trifluoroacetic acid.
2. The process of claim 1 wherein $R^2$ is chloroacetyl.
3. The process of claim 2 wherein $R^2$ is allyloxycarbonyl.
4. The process of claim 3 wherein $R^0$ is hydrogen.
5. The process of claim 4 wherein $R^1$ is hydrogen.
6. The process of claim 4 wherein $R^1$ is halo.
7. The process of claim 6 wherein $R^1$ is chloro.
8. The process of claim 6 wherein $R^1$ is 5-chloro.
9. The process of claim 4 wherein $R^1$ is methoxy.
10. The process of claim 9 wherein $R^1$ is 5-methoxy.

* * * * *